United States Patent [19]

Wolf et al.

[11] Patent Number: 4,831,036
[45] Date of Patent: May 16, 1989

[54] 1,2,3,6-TETRAHYDRO-5-NITRO-PYRIMIDINE DERIVATIVES

[75] Inventors: Hilmar Wolf, Langenfeld; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 52,102

[22] Filed: May 18, 1987

[30] Foreign Application Priority Data

May 30, 1986 [DE] Fed. Rep. of Germany ........ 3618126
Nov. 8, 1986 [DE] Fed. Rep. of Germany ....... 3638121

[51] Int. Cl.$^4$ .................. A61K 31/505; C07D 521/00
[52] U.S. Cl. .................................... 514/258; 514/221; 514/233.2; 514/253; 540/568; 544/117; 544/279; 544/281
[58] Field of Search ................ 544/279, 281; 540/568; 514/117, 221, 253, 258, 233.2

[56] References Cited

U.S. PATENT DOCUMENTS

| 4,031,087 | 6/1977 | Powell | 424/246 |
| 4,394,505 | 7/1983 | Kamata et al. | 544/279 |
| 4,643,999 | 2/1987 | Tully | 544/281 |

FOREIGN PATENT DOCUMENTS 0004173 9/1979 European Pat. Off. .
0154178 9/1985 European Pat. Off. .

Primary Examiner—Glennon H. Hollrah
Assistant Examiner—James H. Turnipseed
Attorney, Agent, or Firm—Sprung Horn Kramer & Woods

[57] ABSTRACT

New 1,2,3,6-tetrahydro-5-nitro-pyrimidine derivatives of the formula

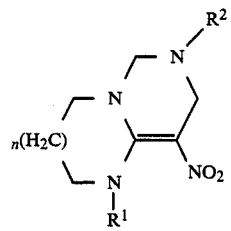

in which
n represents the numbers 0, 1 or 2,
$R^1$ represents hydrogen or optionally substituted radicals from the series comprising alkyl, alkenyl, alkinyl, aralkyl and hetarylalkyl, and
$R^2$ represents dialkylamino, alkoxy, alkenyloxy, aralkoxy or optionally substituted radicals from the series comprising alkyl, alkenyl, alkinyl, cycloalkyl, aralkyl and hetarylalkyl, and their acid addition salts have been found.

It has furthermore been found that these 1,2,3,6-tetrahydro-5-nitor-pyrimidine derivatives have unexpectedly high activity as insecticides, nematicides and ectoparasiticides.

5 Claims, No Drawings

1,2,3,6-TETRAHYDRO-5-NITRO-PYRIMIDINE DERIVATIVES

The present invention relates to new 1,2,3,6-tetrahydro-5-nitro-pyrimidine derivatives a process for their preparation, and their use as pesticides, particularly as insecticides and nematicides. In addition, the new compounds have a strongly developed ectoparasiticidal activity.

It is already known that certain pyrimidino-thiazines, such as, for example, 7-ethyl-9-nitro-3,4,7,8-tetrahydro-(2H,6H)-pyrimidino-[4, 3-b]-1, 3-thiazine, have insecticidal properties (cf. U.S. Pat. No. 4,031,087).

The new 1,2,3,6-tetrahydro-5-nitro-pyrimidine derivatives of the formula (I),

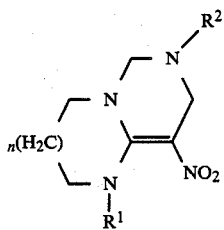

in which
n represents the numbers 0, 1 or 2,
$R^1$ represents hydrogen or optionally substituted radicals from the series comprising alkyl, alkenyl, alkinyl, aralkyl and hetarylalkyl, and
$R^2$ represents dialkylamino, alkoxy, alkenyloxy, aralkoxy or optionally substituted radicals from the series comprising alkyl, alkenyl, alkinyl, cycloalkyl, aralkyl and hetarylalkyl,
and their acid addition salts have now been found.

It has furthermore been found that the 1,2,3,6-tetrahydro-5-nitro-pyrimidine derivatives of the formula (I), and their acid addition salts, are obtained when nitromethylene derivatives of the formula (II)

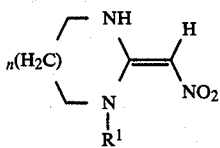

in which
$R^1$ and n have the abovementioned meanings,
are reacted with amines of the formula (III)

$$R^2NH_2 \quad (III)$$

in which
$R^2$ has the abovementioned meanings,
in the presence of at least twice the molar amount of formaldehyde, if appropriate in the presence of acidic catalysts and if appropriate in the presence of diluents, and, if appropriate, physiologically acceptable acids are added to the compounds obtained.

Surprisingly, the 1,2,3,6-tetrahydro-5-nitro-pyrimidine derivatives of the formula (I) according to the invention have unexpectedly high activity as insecticides, nematicides and ectoparasiticides.

The invention preferably relates to compounds of the formula (I), in which n represents the numbers 0, 1 or 2,
$R^1$ represents hydrogen, or alkyl, having 1 to 20 carbon atoms, which is optionally substituted by fluorine, chlorine, bromine, cyano, nitro, hydroxyl, $C_1$–$C_4$-alkoxy, $C_1$–$C_4$-alkylthio, halogeno-$C_1$–$C_2$-alkoxy, halogeno-$C_1$–$C_2$-alkylthio, amino, $C_1$–$C_4$-alkylamino or di-$C_1$–$C_4$-alkylamino; alkenyl and alkinyl each having 2 to 6 carbon atoms; aralkyl, having 6 to 10 carbon atoms in the aryl part and 1 to 4 carbon atoms in the alkyl part, which is optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_2$-alkyl, halogeno-$C_1$–$C_2$-alkoxy or halogeno-$C_1$–$C_2$-alkylthio, or represents furyl-$C_1$–$C_3$-alkyl, thiophenyl-$C_1$–$C_3$-alkyl, pyrazolyl-$C_1$–$C_3$-alkyl, imidazolyl-$C_1$–$C_3$-alkyl, pyrrolyl-$C_1$–$C_3$-alkyl, 1,2,4-triazolyl-$C_1$–$C_3$-alkyl, 1,2,3-triazolyl-$C_1$–$C_3$-alkyl, pyrimidinyl-$C_1$–$C_3$-alkyl, pyrazinyl-$C_1$–$C_3$-alkyl, pyridyl-$C_1$–$C_3$-alkyl, oxazolyl-$C_1$–$C_3$-alkyl, isoxazolyl-$C_1$–$C_3$-alkyl, 1,2,4-oxadiazolyl-$C_1$–$C_3$alkyl, 1,3,4-oxadiazolyl-$C_1$–$C_3$-alkyl, thiazolyl-$C_1$–$C_3$-alkyl, isothiazolyl-$C_1$–$C_3$-alkyl, 1,2,5-thiadiazolyl-$C_1$–$C_3$-alkyl and 1,3,4-thiadiazolyl-$C_1$–$C_3$-alkyl which are optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkylthio, amino, $C_1$–$C_4$-alkylamino or di-$C_1$–$C_4$-alkylamino, and $R^2$ represents dialkylamino having 1 to 6 carbon atoms in each alkyl part; alkoxy having 1 to 6 carbon atoms; alkenyloxy having 3 to 6 carbon atoms; aralkoxy having 6 to 10 carbon atoms in the aryl part and 1 to 4 carbon atoms in the alkyl part, or alkyl, having 1 to 20 carbon atoms, which is optionally substituted by fluorine, chlorine, bromine, cyano, nitro, hydroxyl, mercapto, $C_1$–$C_4$-alkoxy, $C_1$–$C_4$-alkylthio, halogeno-$C_1$–$C_2$-alkoxy, halogeno-$C_1$–$C_2$-alkylthio, amino, $C_1$–$C_4$-alkylamino, di-$C_1$–$C_4$-alkylamino, hydroxycarbonyl, $C_1$–$C_4$-alkoxycarbonyl, $C_1$–$C_4$-alkylcarbonylamino, morpholino or $C_3$–$C_6$-cycloalkyl; alkenyl and alkynyl each having 3 to 6 carbon atoms; cycloalkyl, having 3 to 8 carbon atoms, which is optionally substituted by $C_1$–$C_2$-alkyl, fluorine, chlorine, bromine or halogeno-$C_1$–$C_2$-alkyl; aralkyl, having 6 to 10 carbon atoms in the aryl part and 1 to 4 carbon atoms in the alkyl part, which is optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_2$-alkyl, halogeno-$C_1$–$C_2$-alkoxy or halogeno-$C_1$–$C_2$-alkylthio, and also represents furyl-$C_1$–$C_3$-alkyl, thiophenyl-$C_1$–$C_3$-alkyl, pyrazolyl-$C_1$–$C_3$-alkyl, imidazolyl-$C_1$–$C_3$-alkyl, pyrrolyl-$C_1$–$C_3$-alkyl, 1,2,4-triazolyl-$C_1$–$C_3$-alkyl, 1,2,3-triazolyl-$C_1$–$C_3$-alkyl, pyridyl-$C_1$–$C_3$-alkyl, pyrazinyl-$C_1$–$C_3$-alkyl, pyrimidinyl-$C_1$–$C_3$-alkyl, oxazolyl-$C_1$–$C_3$-alkyl, isoxazolyl-$C_1$–$C_3$-alkyl, 1,2,4-oxadiazolyl-$C_1$–$C_3$-alkyl, 1,3,4-oxadiazolyl-$C_1$–$C_3$-alkyl, thiazolyl-$C_1$–$C_3$-alkyl, isothiazolyl-$C_1$–$C_3$-alkyl, 1,2,5-thiadiazolyl-$C_1$–$C_3$-alkyl and 1,3,4-thiadiazolyl-$C_1$–$C_3$-alkyl which are optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkylthio, amino, $C_1$–$C_4$-alkylamino or di-$C_1$–$C_4$-alkylamino.

Particularly preferred compounds of the formula (I) are those in which n represents the numbers 0 or 1, R¹ represents hydrogen, or alkyl, having 1 to 12 carbon atoms, which is optionally substituted by fluorine, chlorine, cyano, nitro, hydroxyl, methoxy, ethoxy, methylthio, ethylthio, trifluoromethoxy, difluoromethoxy, trichloromethoxy, chlorodifluoromethoxy, trifluoromethylthio, difluoromethylthio, trichloromethylthio, chlorodifluoromethylthio, amino, methylamino, ethylamino, dimethylamino or diethylamino; alkenyl and alkinyl each having 3 or 4 carbon atoms; benzyl and phenylethyl which are optionally substituted by fluorine, chlorine, bromine, cyano, nitro, methyl, ethyl, methoxy, ethoxy, methylthio, ethylthio, trifluoromethyl, trifluoromethoxy or trifluoromethylthio, and also represents thiophenylmethyl, pyrazolylmethyl, 1,2,4-triazolylmethyl, pyrazinylmethyl, pyrimidinylmethyl, pyridylmethyl, isoxazolylmethyl, oxazolylmethyl, thiazolylmethyl, 1,2,5-thiadiazolylmethyl or 1,3,4-thiadiazolylmethyl which are optionally substituted by fluorine, chlorine, bromine, cyano, nitro, methyl, ethyl, methoxy, methylthio, trifluoromethyl, trifluoromethoxy, trifluoromethylthio, dimethylamino or diethylamino, and R² represents dialkylamino having 1 to 4 carbon atoms in each alkyl part; alkoxy having 1 to 4 carbon atoms; 1-prop-2-enyloxy; phenylmethoxy, phenylethoxy; alkyl, having 1 to 12 carbon atoms, which is optionally substituted by fluorine, chlorine, bromine, cyano, nitro, hydroxyl, mercapto, methoxy, ethoxy, methylthio, ethylthio, trifluoromethoxy, difluoromethoxy, trichloromethoxy, chlorodifluoromethoxy, trifluoromethylthio, difluoromethylthio, trichloromethylthio, chlorodifluoromethylthio, amino, methylamino, ethylamino, dimethylamino, diethylamino, hydroxycarbonyl, $C_1$–$C_2$-alkoxycarbonyl, $C_1$–$C_2$-alkylcarbonylamino or $C_3$–$C_6$-cycloalkyl; alkenyl and alkinyl each having 3 or 4 carbon atoms; cycloalkyl, having 3 to 6 carbon atoms, which is optionally substituted by fluorine, chlorine or trifluoromethyl; benzyl and phenylethyl which are optionally substituted by fluorine, chlorine, bromine, cyano, nitro, methyl, ethyl, methoxy, ethoxy, methylthio, ethylthio, trifluoromethyl, trifluoromethoxy or trifluoromethylthio, and also represents furylmethyl, thiophenylmethyl, pyrrolylmethyl, pyrimidinylmethyl, thiazolylmethyl, pyrazolylmethyl, morpholinomethyl or morpholino-n-propyl which are optionally substituted by fluorine, chlorine, bromine, cyano, nitro, methyl, ethyl, methoxy, methylthio, trifluoromethyl, trifluoromethoxy, trifluoromethylthio, dimethylamino or diethylamino.

Preferred compounds according to the invention are also addition products of acids and those 1,2,3,6-tetrahydro-5-nitro-pyrimidine derivatives of the formula (I) in which the substituents R, R¹ and R² or the index n, have the meanings which have already been preferably mentioned for these substituents and the index.

The acids which may be added preferably include hydrohalic acids, such as, for example, hydrochloric acid and hydrobromic acid, particularly hydrochloric acid, furthermore phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, phthalic acid, naphthalenesulphonic acid, nicotinic acid, citric acid and ascorbic acid.

For example, 3-methyl-2-nitromethylene-imidazolidine, cyclohexylamine and at least twice the molar amount of formaldehyde are used as starting materials for the process according to the invention, and the corresponding reaction can thus be represented by the following equation:

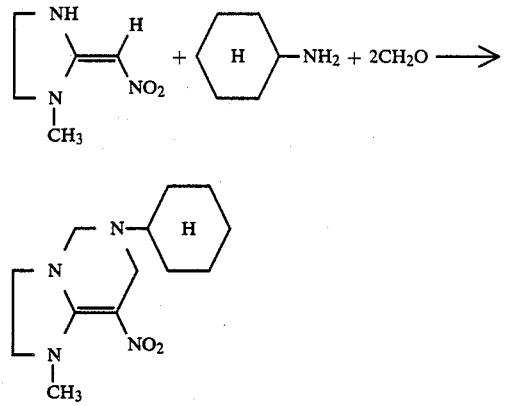

The nitromethylene derivatives to be used as starting materials in the process according to the invention are generally defined by the formula (II). In this formula (II), R¹ and n preferably represent those radicals which have already been mentioned in connection with the description of the substances of the formula (I) according to the invention as being preferred for this substituent and the index.

The compounds of the formula (II) are known and/or can be prepared by known methods (cf., for example, DE-OS (German Published Specification) No. 2,514,402, EP-OS (European Published Specification) No. 136,636, EP-OS (European Published Specification) No. 154,178 and EP-OS (European Published Specification) No. 163,855).

The following may be mentioned as examples of compounds of the formula (II):

TABLE 1

| n | R¹ | n | R¹ |
|---|----|---|----|
| 0 | H | 0 | CH₃ |
| 0 | C₂H₅ | 0 | —CH₂—(2-chloropyridyl) |
| 0 | —CH₂—(pyridyl) | 0 | —CH₂—(4-chlorophenyl) |

TABLE 1-continued $$\underset{R^1}{\underset{|}{N}}\overset{NH}{\underset{\diagdown}{\diagup}}C=C\overset{H}{\underset{NO_2}{\diagdown}}$$

with n(H₂C) bridging

| n | R¹ | n | R¹ |
|---|---|---|---|
| 0 | —CH₂—C₆H₅ | 0 | —CH₂CH₂CN |
| 0 | —CH₂—CH=CH₂ | 0 | —CH₂—C≡CH |
| 0 | —CH₂-(2-thienyl) | 0 | —CH₂—C(S)=N—Cl (allyl-type) |
| 0 | —CH₂-(thiadiazolyl-Cl) | 0 | —CH₂-(pyrazolyl-N-CH₃) |
| 1 | H | 1 | CH₃ |
| 1 | C₂H₅ | 1 | —CH₂-(6-Cl-pyridin-3-yl) |
| 1 | —CH₂-(pyridin-3-yl) | 1 | —CH₂-(4-Cl-C₆H₄) |
| 1 | —CH₂—C₆H₅ | 1 | —CH₂CH₂CN |
| 1 | —CH₂—CH=CH₂ | 1 | —CH₂—C≡CH |
| 1 | —CH₂-(2-thienyl) | 1 | —CH₂—C(S)=N—Cl |
| 1 | —CH₂-(thiadiazolyl-Cl) | 2 | H |
| 0 | —CH₂-(6-CH₃-pyrazin-3-yl) | 0 | —CH₂-(pyrimidinyl) |
| 0 | —CH₂-(isoxazolyl) | | |

The amines additionally to be used as starting materials in the process according to the invention are generally defined by the formula (III). In this formula (III), R² preferably represents those radicals which have already been mentioned in connection with the description of the substances of the formula (I) according to the invention as being preferred for this substituent.

The amines of the formula (III) are generally known compounds of organic chemistry.

The following may be mentioned as examples of compounds of the formula (III):

TABLE 2

R²NH₂ (III)

| R² | R² |
|---|---|
| —CH₃ | —C₂H₅ |
| —C₃H₇—n | —C₃H₇—i |
| —C₄H₉—n | —C₄H₉—i |
| —C₄H₉—sec. | —C₄H₉—tert. |
| —CH(CH₃)—C(CH₃)₃ | —HC(cyclopropyl) |
| —C₆H₁₁ (cyclohexyl) | —N(CH₃)₂ |
| —N(C₂H₅)₂ | —N(C₃H₇—n)₂ |
| —CH₂—CH=CH₂ | —CH₂—C≡CH |
| —CH₂CH₂OH | —CH₂CH₂N(CH₃)₂ |
| —CH₂CH₂N(C₂H₅)₂ | —CH₂CH₂N(C₃H₇—n)₂ |
| —CH₂—C₆H₅ | —CH₂—C₆H₄—Cl |
| —CH₂-(pyridin-3-yl) | —CH₂-(6-Cl-pyridin-3-yl) |
| -(4-CF₃-cyclohexyl) | -(CF₃,CH₃-cyclohexyl) |
| —HC(CH₂)(CH—CF₃) cyclopropyl | —HC(CH₂)(C(CH₃)₂) cyclopropyl |
| —HC(CH₂)(CCl₂) cyclopropyl | -(4-Cl-cyclohexyl) |
| —CH₂CH₂CN | —(CH₂)₅—CH₃ |
| —(CH₂)₄—CH₃ | —(CH₂)₁₁—CH₃ |
| —(CH₂)₁₅—CH₃ | —CH₂CH₂—OCH₃ |
| —CH₂CH₂CH₂OCH₃ | —(CH₂)₃O(CH₂)₃CH₃ |
| —CH₂-(3-Cl-C₆H₄) | —CH₂-(2-thienyl) |

TABLE 2-continued

R²NH₂      (III)

| R² | R² |
|---|---|
| —CH₂—(furan-2-yl) | —CH₂CH₂—(N-methylpyrrol-2-yl) |
| —CH₂—C(=O)—OC₂H₅ | —CH₂—(cyclohexyl, H) |
| —CH₂CH₂CH₂—N(morpholino) | —CH₂CH₂CH₂OH |
| —CH₂CH₂CH₂Cl | —CH₂CH₂SH |
| —CH₂CF₃ | —CH(CH₃)(CF₃) |
| —CH₂CH(OCH₃)₂ | —CH₂CH₂CO₂C₂H₅ |
| —CH₂CH₂NHC(=O)CH₃ | —CH₂CO₂H |
| —CH₂CH₂CO₂H | —OCH₃ |
| —OC₂H₅ | —OCH₂CH=CH₂ |
| —OCH₂—(phenyl) | |

The process according to the invention for the preparation of the new compounds of the formula (I) is preferably carried out using diluents. Suitable diluents are water and inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, and alcohols, such as methanol, ethanol, n-propanol and isopropanol. Mixtures of alcohols and water are preferably employed.

The process according to the invention is optionally carried out in the presence of acidic, non-oxidizing catalysts. Hydrohalic acids such as hydrochloric acid and hydrobromic acid, phosphoric acid, and lower carboxylic acids such as acetic acid and propionic acid have proven themselves in particular.

The reaction temperatures may be varied within a relatively wide range in the process according to the invention. In general, the reaction is carried out at temperatures between $-20°$ C. and $+120°$ C., preferably at temperatures between $0°$ C. and $+80°$ C.

The process according to the invention is generally carried out at atmospheric pressure. However, it is also possible to carry out the process at increased or reduced pressure.

To carry out the process according to the invention, 1 to 1.5 mole, preferably 1 to 1.2 mole, of amine of the formula (III) and 2 to 4 mole, preferably 2 to 3 mole, of formaldehyde are employed per mole of nitromethylene derivative of the formula (II).

The amines of the formula (III) can, if appropriate, be employed as aqueous solutions. When using gaseous amines of the formula (III), these compounds can be passed through the mixture of diluent, compounds of the formula (II) and formaldehyde. Formaldehyde is employed in aqueous solution for the process according to the invention. The reactions are generally carried out in a suitable diluent, and the reaction mixture is stirred for several hours at the temperature necessary in each case. Working up in the process according to the invention occurs by conventional methods in each case.

The acid addition salts of the compounds of the formula (I) can be obtained in a simple fashion by conventional salt-formation methods, for example by dissolution of a compound of the formula (I) in a suitable inert solvent and addition of the acid, for example hydrochloric acid, and isolation in a known fashion, for example by filtering off, and, if necessary, purification by washing with an inert organic solvent.

The active compounds are suitable for combating animal pests, in particular insects and nematodes, which are encountered in agriculture, in forestry, in the protection of stored products and of materials, and in the hygiene field, and have good plant tolerance and favorable toxicity to warm-blooded animals. They are active against normally sensitive and resistant species and against all or some stages of pest development. The abovementioned pests include:

From the order of the Isopoda, for example, Oniscus asellus, Armadillidium vulgare and Porcellio scaber. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex Lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae. Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusiani, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psyllioides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrusspp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphoaptera, for example, *Xenopsylla cheopis* and Ceratophyllus spp. From the order of the Arachnida, for example, *Scorpio maurus* and *Latrodectus mactans.*

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds of the formula (I) according to the invention are distinguished by an excellent insecticidal and nematicidal activity. Particularly when used as leaf insecticides and soil insecticides, they exhibit an excellent action against grubs such as, for example, Phorbia antiqua grubs, against caterpillars, such as, for example, *Plutella maculipennis,* against beetle larvae, such as, for example, *Phaedon cochleariae* and *Diabrotica balteata,* and against aphids, such as, for example, *Myzus persicae* and *Aphis fabae.* In addition, they also exhibit a very good activity when used against nematodes, such as, for example, *Meloidogyne incognita.*

The new compounds are thus particularly well suited for combating leaf insects, soil insects and nematodes.

In addition, the new compounds display a bactericidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks etc. in the sectors of animal keeping and cattle breeding; better results, for example higher milk production, greater weight, more attractive animal pelt, longer life etc., can be achieved by combating the pests. Particularly when used as ectoparasiticides, they exhibit an excellent action against blowfly larvae, such as Lucilia cuprina.

The application of the active compounds according to the invention occurs in this sector in a known fashion, by means of external application in the form of, for example, dipping, spraying, pouring-on, spotting-on and dusting.

The biological effectiveness of the compounds according to the invention will be explained with reference to the examples below.

PREPARATION EXAMPLES

EXAMPLE 1

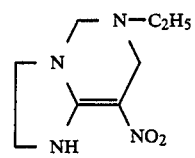

16.8 ml (0.22 mole) of 30% strength aqueous formaldehyde solution is added dropwise, over 1 hour at 5° C.–10° C., to a mixture of 12.9 g (0.1 mole) of 2-nitromethyleneimidazoline and 7.1 g (0.11 mole) of a 70% strength aqueous solution of ethylamine in 50 ml of ethanol and 30 ml of water. The reaction mixture is subsequently stirred for 16 hours at 25° C., and the solvent is removed by distillation in vacuo. The residue is recrystallized from ethyl acetate.

17.8 g (89% of theory) of 6,7-dihydro-6-ethyl-8-nitro-(5H)-imidazolidino-[2,3,-f]-pyrimidine are thus obtained as beige crystals of melting point 159° C.

The compounds of the formula (I) specified in the Table 3 below can be prepared analogously to Example 1 or to the process according to the invention:

TABLE 3

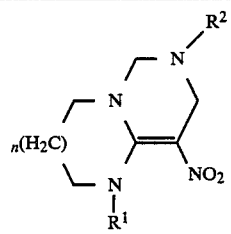

| Example No. | n | $R^1$ | $R^2$ | Physical constants |
|---|---|---|---|---|
| 2 | 0 | H | —CH$_2$—C$_6$H$_5$ (benzyl) | M.p.: 186° C. |
| 3 | 0 | H | —CH$_2$CH$_2$—N(C$_2$H$_5$)$_2$ | M.p.: 122° C. |
| 4 | 0 | H | —CH$_2$—(pyridyl) | M.p.: 208° C. |
| 5 | 0 | H | —CH$_2$—C$_6$H$_4$—Cl | M.p.: 148° C. |
| 6 | 0 | H | —CH(CH$_3$)—C(CH$_3$)$_3$ | *δ = 4.06 (s) |
| 7 | 0 | H | —CH$_3$ | M.p.: 166° C. |
| 8 | 0 | H | —C$_3$H$_7$—i | M.p.: 146° C. |

TABLE 3-continued

[Structure: bicyclic ring containing N-R², N, n(H₂C), N-R¹, and =NO₂ group]

| Example No. | n | R¹ | R² | Physical constants |
|---|---|---|---|---|
| 9 | 0 | −CH₂−(3-pyridyl) | −C₃H₇−i | M.p.: 136–138° C. |
| 10 | 1 | H | −C₃H₇−i | M.p.: 150–152° C. |
| 11 | 0 | −CH₂−(3-pyridyl) | −C₂H₅ | M.p.: 142° C. |
| 12 | 1 | H | −C₂H₅ | M.p.: 140–142° C. |
| 13 | 0 | −CH₂−(3-pyridyl) | −CH₃ | M.p.: 189° C. |
| 14 | 1 | H | −CH₃ | M.p.: 188° C. |
| 15 | 0 | −CH₂−(6-chloro-3-pyridyl) | −C₃H₇−i | M.p.: 136–138° C. |
| 16 | 0 | −CH₂−(6-chloro-3-pyridyl) | −CH₃ | M.p.: 150–152° C. |
| 17 | 1 | −CH₃ | −CH₃ | M.p.: 120–122° C. |
| 18 | 1 | −CH₃ | −C₃H₇−i | M.p.: 124–128° C. |
| 19 | 1 | −CH₃ | −C₃H₇−n | M.p.: 130–132° C. |
| 20 | 0 | −CH₂CH₂CN | −CH₃ | M.p.: 152–155° C. |
| 21 | 0 | −CH₂CH₂CN | −C₂H₅ | M.p.: 156–158° C. |
| 22 | 0 | −CH₂CH₂CN | −C₃H₇−i | M.p.: 163–165° C. |
| 23 | 0 | −CH₂CH₂CN | −C₃H₇−n | M.p.: 129° C. |
| 24 | 0 | −CH₂−(4-chlorophenyl) | −CH₃ | M.p.: 156–158° C. |
| 25 | 0 | −CH₂−(4-chlorophenyl) | −C₂H₅ | M.p.: 180–182° C. |
| 26 | 0 | −CH₂−(4-chlorophenyl) | −C₃H₇−i | M.p.: 150–151° C. |
| 27 | 0 | −CH₂−(4-chlorophenyl) | −C₃H₇−n | M.p.: 166° C. |

TABLE 3-continued
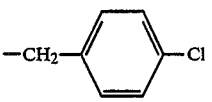
| Example No. | n | R¹ | R² | Physical constants |
|---|---|---|---|---|
| 28 | 1 | 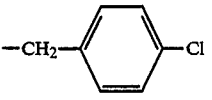 -CH₂-⟨C₆H₄⟩-Cl | —CH₃ | M.p.: 168–170° C. |
| 29 | 1 | -CH₂-⟨C₆H₄⟩-Cl | —C₂H₅ | M.p.: 156–158° C. |
| 30 | 1 | -CH₂-⟨C₆H₄⟩-Cl | —C₃H₇—i | M.p.: 140° C. |
| 31 | 1 | -CH₂-⟨C₆H₄⟩-Cl | —C₃H₇—n | M.p.: 138–140° C. |
| 32 | 2 | H | —C₂H₅ | M.p.: 100–108° C. |
| 33 | 1 | —CH₂CH₂CN | —CH₃ | M.p.: 156° C. |
| 34 | 1 | -CH₂-⟨4-pyridyl⟩ | —CH₃ | M.p.: 136° C. |
| 35 | 1 | -CH₂-⟨6-Cl-3-pyridyl⟩ | —CH₃— | M.p.: 142° C. |
| 36 | 2 | H | —CH₃ | M.p.: 136–140° C. |
| 37 | 0 | -CH₂-⟨6-Cl-3-pyridyl⟩ | —C₂H₅ | M.p.: 178° C. |
| 38 | 0 | -CH₂-⟨6-Cl-3-pyridyl⟩ | —C₄H₉—tert. | M.p.: 128° C. |
| 39 | 0 | -CH₂-⟨6-Cl-3-pyridyl⟩ | —CH₂CH₂OH | M.p.: 160–162° C. |
| 40 | 0 | -CH₂-⟨6-Cl-3-pyridyl⟩ | cyclohexyl | M.p.: 168° C. |

TABLE 3-continued

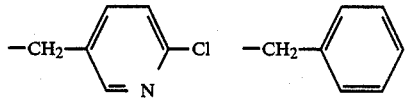

| Example No. | n | R¹ | R² | Physical constants |
|---|---|---|---|---|
| 41 | 0 | -CH₂-(6-chloropyridin-3-yl) | -CH₂-C₆H₅ | M.p.: 150–152° C. |
| 42 | 0 | -CH₂-(6-chloropyridin-3-yl) | -HC(CH₂)(CH₃) (cyclopropyl-methyl type) | M.p.: 150° C. |
| 43 | 1 | -CH₂-(6-chloropyridin-3-yl) | -C₂H₅ | M.p.: 144° C. |
| 44 | 1 | -CH₂-(6-chloropyridin-3-yl) | -C₃H₇-i | M.p.: 142° C. |
| 45 | 1 | -CH₂-(6-chloropyridin-3-yl) | -HC(CH₂)(CH₃) | M.p.: 82° C. |
| 46 | 0 | -CH₂-(6-chloropyridin-3-yl) | -CH₂-CH=CH₂ | M.p.: 144° C. |
| 47 | 1 | -CH₃ | -CH₂-(6-chloropyridin-3-yl) | M.p.: 176° C. |
| 48 | 0 | H | -C₄H₉-n | M.p.: 122° C. |
| 49 | 0 | H | -C₆H₁₃-n | M.p.: 112° C. |
| 50 | 0 | H | -CH₂CH₂OCH₃ | M.p.: 109° C. |
| 51 | 0 | H | -CH₂CH₂CH₂OCH₃ | M.p.: 106° C. |
| 52 | 0 | -CH₂-(6-chloropyridin-3-yl) | -C₄H₉-n | M.p.: 134° C. |
| 53 | 0 | -CH₂-(6-chloropyridin-3-yl) | -C₆H₁₃-n | M.p.: 134° C. |
| 54 | 0 | -CH₂-(6-chloropyridin-3-yl) | -CH₂CH₂OCH₃ | M.p.: 169° C. |

TABLE 3-continued

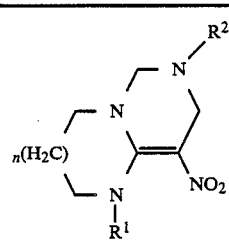

| Example No. | n | R¹ | R² | Physical constants |
|---|---|---|---|---|
| 55 | 0 | —CH₂—(2-Cl-pyridin-5-yl) | —CH₂—(4-Cl-phenyl) | M.p.: 186° C. |
| 56 | 0 | —CH₂—(2-Cl-pyridin-5-yl) | —CH₂—(2-Cl-phenyl) | M.p.: 94° C. |
| 57 | 0 | —CH₂—(2-Cl-pyridin-5-yl) | —C₁₂H₂₅—n | M.p.: 117° C. |
| 58 | 0 | —CH₂—(2-Cl-pyridin-5-yl) | —C₅H₁₁—n | M.p.: 129° C. |
| 59 | 0 | —CH₂—(2-Cl-pyridin-5-yl) | —C₁₆H₃₃—n | M.p.: 122° C. |
| 60 | 0 | —CH₂—(2-Cl-pyridin-5-yl) | —(CH₂)₃—O—(CH₂)₃CH₃ | M.p.: 78° C. |
| 61 | 0 | —CH₂—(2-Cl-pyridin-5-yl) | —CH₂CH₂—N(C₂H₅)₂ | M.p.: 125° C. |
| 62 | 0 | —CH₂—(2-Cl-pyridin-5-yl) | —CH₂—(pyridin-3-yl) | M.p.: 134° C. |
| 63 | 0 | —CH₂—(2-Cl-pyridin-5-yl) | —CH₂CH₂CH₂—N(morpholino) | M.p.: 120° C. |
| 64 | 0 | —CH₂—(2-Cl-pyridin-5-yl) | —CH₂—(furan-2-yl) | M.p.: 160° C. |

TABLE 3-continued
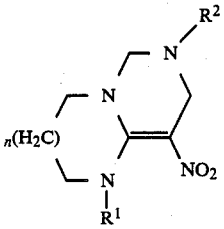
| Example No. | n | R¹ | R² | Physical constants |
|---|---|---|---|---|
| 65 | 0 | 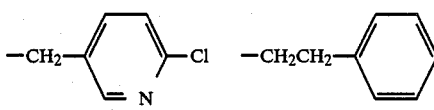—CH₂—(2-Cl-pyridin-5-yl) | —CH₂CH₂—C₆H₅ | M.p.: 114° C. |
| 66 | 0 | 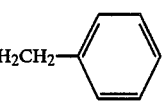—CH₂—(2-Cl-pyridin-5-yl) | —CH₂CH(OCH₃)₂ | M.p.: 150° C. |
| 67 | 0 | 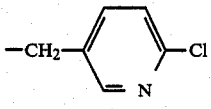—CH₂—(2-Cl-pyridin-5-yl) | —CH₂—(thien-2-yl) | M.p.: 158° C. |
| 68 | 0 | 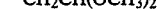—CH₂—(2-Cl-pyridin-5-yl) | —CH₂CH₂COOC₂H₅ | |
| 69 | 0 | 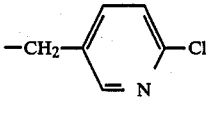—CH₂—(2-Cl-pyridin-5-yl) | —CH₂CH₂CH₂Cl | M.p.: 120° C. |
| 70 | 0 | 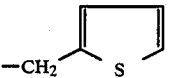—CH₂—(2-Cl-pyridin-5-yl) | —CH₂CH₂SH | |
| 71 | 0 | 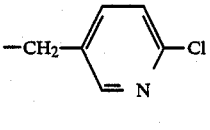—CH₂—(2-Cl-pyridin-5-yl) | —N(CH₃)₂ | |
| 72 | 0 | —CH₂—(thien-2-yl) | —CH₃ | M.p.: 112° C. |
| 73 | 1 | 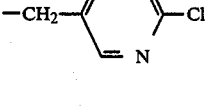—CH₂—(thien-2-yl) | —CH₃ | |
| 74 | 0 | —CH₂—(2-Cl-thiazol-5-yl) | —CH₃ | *δ = 4.95 (s) |
| 75 | 1 | 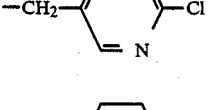—CH₂—(2-Cl-thiazol-5-yl) | —CH₃ | *δ = 4.66 (s) |

TABLE 3-continued

Structure: piperazine-type ring with n(H2C) bridge, N-R1, N-R2, and =NO2 substituent

| Example No. | n | R¹ | R² | Physical constants |
|---|---|---|---|---|
| 76 | 0 | -CH₂-(1,3,4-thiadiazol-2-yl with Cl) | -CH₃ | |
| 77 | 1 | -CH₂-(1,3,4-thiadiazol-2-yl with Cl) | -CH₃ | |
| 78 | 0 | -CH₂-(6-chloropyridin-3-yl) | -CH₂-cyclohexyl | M.p.: 150° C. |
| 79 | 0 | -CH₂-(6-chloropyridin-3-yl) | -CH₂COOC₂H₅ | M.p.: 147° C. |
| 80 | 0 | -CH₂-(6-chloropyridin-3-yl) | -CH₂CH₂NH-COCH₃ | |
| 81 | 0 | -CH₂-(6-chloropyridin-3-yl) | -CH₂COOH | M.p.: 88° C. |
| 82 | 0 | -CH₂-(6-chloropyridin-3-yl) | -CH₂CH₂COOH | |
| 83 | 0 | -CH₂-(6-chloropyridin-3-yl) | -OCH₃ | |
| 84 | 0 | -CH₂-(6-chloropyridin-3-yl) | -OC₂H₅ | |
| 85 | 0 | -CH₂-(6-chloropyridin-3-yl) | -OCH₂CH=CH₂ | |
| 86 | 0 | -CH₂-(6-chloropyridin-3-yl) | -OCH₂-phenyl | |

TABLE 3-continued

[Structure: bicyclic ring system with N-R², N-R¹, n(H₂C), and =NO₂ group]

| Example No. | n | R¹ | R² | Physical constants |
|---|---|---|---|---|
| 87 | 0 | —CH₂—(6-chloropyridin-3-yl) | —CH₂CF₃ | M.p.: 143° C. |
| 88 | 0 | —CH₂—(6-chloropyridin-3-yl) | —CH(CH₃)(CF₃) | M.p.: 163° C. |
| 89 | 1 | —CH₂—(6-chloropyridin-3-yl) | —CH₂C≡CH | *δ = 4.60 (s) |
| 90 | 0 | —CH₂—(6-chloropyridin-3-yl) | —CH₂CH₂CH₂OCH₃ | M.p.: 181° C. |
| 91 | 0 | —CH₂—(6-chloropyridin-3-yl) | —CH₂CH₂CH₂OH | M.p.: >230° C. |
| 92 | 0 | —CH₂—(6-chloropyridin-3-yl) | —CH₂CH(OH)—CH₃ | M.p.: 146° C. |
| 93 | 0 | —CH₂—(6-chloropyridin-3-yl) | —CH₂CH₂CN | M.p.: 87° C. |
| 94 | 0 | —CH₂—(6-chloropyridin-3-yl) | —C(CH₃)₂CH₂CH₃ | M.p.: 126° C. |
| 95 | 0 | —CH₂—(6-chloropyridin-3-yl) | —CH(CH₃)COOH | *δ = 4.74 (q) |
| 96 | 0 | —CH₂—(thiophen-2-yl) | —C(CH₃)₂CH₂CH₃ | *δ = 4.98 (s) |
| 97 | 0 | —CH₂—(thiophen-2-yl) | —CH₂CH=CH₂ | M.p.: 104° C. |

TABLE 3-continued

[Structure: piperazine-type ring system with $n(H_2C)$, $R^1$, $R^2$ substituents and $NO_2$ group]

| Example No. | n | R¹ | R² | Physical constants |
|---|---|---|---|---|
| 98 | 0 | $-CH_2-$(2-thienyl) | $-CH_2-$phenyl | M.p.: 164° C. |
| 99 | 0 | $-CH_2-$(2-thienyl) | $-C_2H_5$ | M.p.: 177° C. |
| 100 | 0 | $-CH_2-$(6-chloropyridin-3-yl) | $-C(CH_2F)_2CH_3$ | M.p.: 164° C. |
| 101 | 0 | $-CH_2-$(6-chloropyridin-3-yl) | $-CH(CH_3)-C(CH_3)_3$ | M.p.: 156° C. |
| 102 | 0 | $-CH_2-$(6-chloropyridin-3-yl) | $-CH_2C(CH_3)_3$ | M.p.: 150° C. |
| 103 | 0 | $-CH_2-$(6-chloropyridin-3-yl) | $-CH(CH_3)-CH(CH_3)_2$ | M.p.: 122° C. |
| 104 | 0 | $-CH_2-$(6-chloropyridin-3-yl) | $-CH(CH_3)-$phenyl (R) | M.p.: 131° C. |
| 105 | 0 | $-CH_2-$(6-chloropyridin-3-yl) | $-CH(CH_3)-$phenyl (S) | M.p.: 132° C. |
| 106 | 0 | $-CH_2-$(6-chloropyridin-3-yl) | $-CH(CH_3)-C_2H_5$ | M.p.: 152° C. |
| 107 | 0 | $-CH_2-$(6-chloropyridin-3-yl) | $-CH_2CH(CH_3)_2$ | M.p.: 138° C. |
| 108 | 0 | $-CH_2-$(6-chloropyridin-3-yl) | $-C_3H_7-n$ | M.p.: 172° C. |

TABLE 3-continued
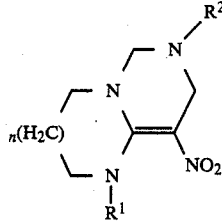
| Example No. | n | R¹ | R² | Physical constants |
|---|---|---|---|---|
| 109 | 0 | 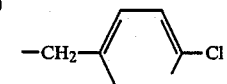 |  | M.p.: 131° C. |
| 110 | 0 | 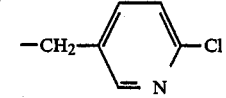 |  | M.p.: 115° C. |
| 111 | 0 | 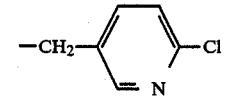 | —CH$_2$CH$_2$OC$_2$H$_5$ | M.p.: 146° C. |
| 112 | 0 |  | 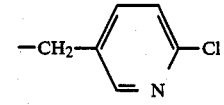 | M.p.: 134° C. |
| 113 | 0 |  | 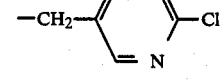 | M.p.: 110° C. |
| 114 | 0 | 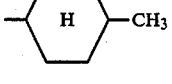 | 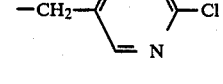 | M.p.: 148° C. |
| 115 | 0 |  | 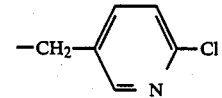 | M.p.: 133° C. |
| 116 | 0 |  | 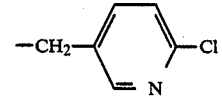 | M.p.: 134° C. |
| 117 | 0 |  | —C(CH$_3$)$_2$CH$_2$CH$_3$ | M.p.: 127° C. |
| 118 | 1 | 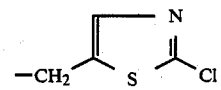 | —C(CH$_3$)$_2$CH$_2$CH$_3$ | M.p.: 149° C. |

TABLE 3-continued
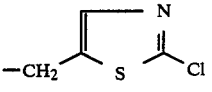
| Example No. | n | R¹ | R² | Physical constants |
|---|---|---|---|---|
| 119 | 0 |  | 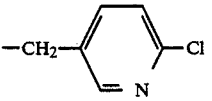 | *δ = 4.92 (s) |
| 120 | 0 | 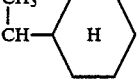 | 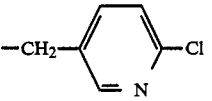 | M.p.: 133° C. |
| 121 | 0 |  | 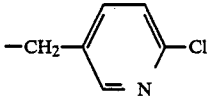 | M.p.: 142° C. |
| 122 | 0 | 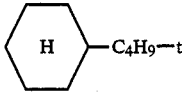 | 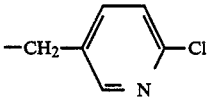 | M.p.: 172° C. |
| 123 | 0 | 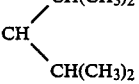 | 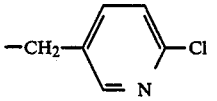 | M.p.: 114° C. |
| 124 | 0 | 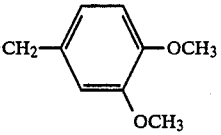 | 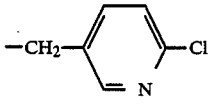 | M.p.: 115° C. |
| 125 | 0 |  | $-CH_2CH_2SC_2H_5$ | M.p.: 180° C. |
| 126 | 0 | 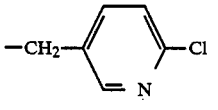 | $-(CH_2)_6CH_3$ | M.p.: 147° C. |
| 127 | 0 |  | $-(CH_2)_7CH_3$ | M.p.: 147° C. |
| 128 | 0 | 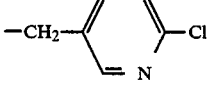 | $-(CH_2)_8CH_3$ | M.p.: 129° C. |

TABLE 3-continued

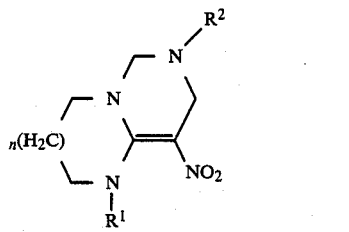

| Example No. | n | R¹ | R² | Physical constants |
|---|---|---|---|---|
| 129 | 0 | —CH₂-(6-chloropyridin-3-yl) | —(CH$_2$)$_9$CH$_3$ | M.p.: 117° C. |
| 130 | 0 | —CH₂-(6-chloropyridin-3-yl) | —(CH$_2$)$_{10}$CH$_3$ | M.p.: 115° C. |
| 131 | 0 | —CH₂-(6-chloropyridin-3-yl) | —(CH$_2$)$_{13}$CH$_3$ | M.p.: 120° C. |
| 132 | 0 | —CH₂-(6-chloropyridin-3-yl) | —CH$_2$—CH(C$_2$H$_5$)—(CH$_2$)$_3$CH$_3$ | M.p.: 119° C. |
| 133 | 0 | —CH₂-(6-chloropyridin-3-yl) | —(CH$_2$)$_{17}$CH$_3$ | M.p.: 120° C. |
| 134 | 0 | —CH₂-(2-chlorothiazol-5-yl) | —CH(CH$_3$)—C(CH$_3$)$_3$ | M.p.: 142° C. |
| 135 | 0 | —CH₂-(2-chlorothiazol-5-yl) | —CH$_2$CH(OCH$_3$)$_2$ | M.p.: 124° C. |
| 136 | 1 | —CH₂-(2-chlorothiazol-5-yl) | —CH(CH$_3$)—C(CH$_3$)$_3$ | M.p.: 144° C. |
| 137 | 1 | —CH₂-(2-chlorothiazol-5-yl) | —(CH$_2$)$_{11}$CH$_3$ | M.p.: 103° C. |
| 138 | 1 | —CH₂-(2-chlorothiazol-5-yl) | —(CH$_2$)$_5$CH$_3$ | M.p.: 76° C. |
| 139 | 1 | —CH₂-(2-chlorothiazol-5-yl) | —(CH$_2$)$_6$CH$_3$ | M.p.: 89° C. |
| 140 | 1 | —CH₂-(2-chlorothiazol-5-yl) | —(CH$_2$)$_7$CH$_3$ | M.p.: 79° C. |

TABLE 3-continued

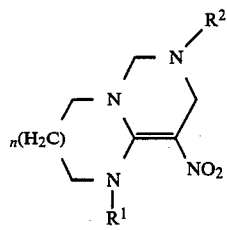

| Example No. | n | R¹ | R² | Physical constants |
|---|---|---|---|---|
| 141 | 1 | -CH₂-C(=CH-N)-S-C-Cl | $-(CH_2)_8CH_3$ | M.p.: 70° C. |
| 142 | 1 | -CH₂-C(=CH-N)-S-C-Cl | $-(CH_2)_9CH_3$ | M.p.: 89° C. |
| 143 | 0 | -CH₂-C(=CH-N)-S-C-Cl | $-(CH_2)_5CH_3$ | M.p.: 75° C. |
| 144 | 0 | -CH₂-C(=CH-N)-S-C-Cl | $-(CH_2)_{11}CH_3$ | M.p.: 81° C. |
| 145 | 0 | -CH₂-C(=CH-N)-S-C-Cl | $-(CH_2)_{17}CH_3$ | M.p.: 89° C. |
| 146 | 0 | -CH₂-C(=CH-N)-S-C-Cl | $-(CH_2)_{10}CH_3$ | M.p.: 104° C. |
| 147 | 0 | -CH₂-C(=CH-N)-S-C-Cl | $-(CH_2)_6CH_3$ | M.p.: 114° C. |
| 148 | 0 | -CH₂-C(=CH-N)-S-C-Cl | $-(CH_2)_{13}CH_3$ | M.p.: 111° C. |
| 149 | 0 | -CH₂-C(=CH-N)-S-C-Cl | $-(CH_2)_{15}CH_3$ | M.p.: 111° C. |
| 150 | 0 | -CH₂-C(=CH-N)-S-C-Cl | $-(CH_2)_7CH_3$ | M.p.: 120° C. |
| 151 | 0 | -CH₂-C(=CH-N)-S-C-Cl | $-(CH_2)_8CH_3$ | M.p.: 111° C. |
| 152 | 0 | -CH₂-C(=CH-N)-S-C-Cl | $-(CH_2)_9CH_3$ | M.p.: 103° C. |
| 153 | 0 | -CH₂-C(=CH-N)-S-C-Cl | $-(CH_2)_8CH=CH(CH_2)_7CH_3$ | M.p.: 82° C. |

TABLE 3-continued

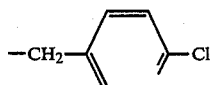

| Example No. | n | R¹ | R² | Physical constants |
|---|---|---|---|---|
| 154 | 0 | −CH₂−(2-Cl-pyridin-5-yl) | −(CH₂CH₂O)₄H | M.p.: 101° C. |
| 155 | 0 | −CH₂−(2-Cl-pyridin-5-yl) | −(CH₂CH₂O)₂CH₃ | M.p.: 118° C. |
| 156 | 0 | −CH₂−(2-Cl-pyridin-5-yl) | −CH₂−CH₂OCH₂CH₂−N(CH₃)₂ | M.p.: 115° C. |
| 157 | 0 | −CH₂−(2-Cl-pyridin-5-yl) | −(CH₂CH₂O)₂C₄H₉ | M.p.: 118° C. |
| 158 | 0 | −CH₂−(2-Cl-pyridin-5-yl) | −(CH₂CH₂O)₂C₂H₅ | M.p.: 160° C. |
| 159 | 0 | −CH₂−(2-Cl-pyridin-5-yl) | −(CH₂CH₂O)₃H | M.p.: 135° C. |
| 160 | 0 | −CH₂−(2-Cl-pyridin-5-yl) | −(CH₂CH₂O)₃CH₃ | M.p.: 110° C. |
| 161 | 0 | −CH₂−(2-Cl-pyridin-5-yl) | −(CH₂CH₂O)₂H− | M.p.: 140° C. |
| 162 | 0 | −CH₂−(2-Cl-pyridin-5-yl) | −(CH₂)₈CH=CH(CH₂)₇CH₃ | M.p.: 95° C. |

*are the values of the ¹H—NMR spectra, which were recorded in CDCl₃.
The chemical shifts for the −CH₂−C(NO₂)=. group are stated.

USE EXAMPLES

In the following use examples, the following compound was employed as comparison substance:

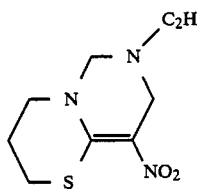

(A)

7-Ethyl-9-nitro-3,4,7,8-tetrahydro-(2H,6H)-pyrimidino-[4,3-b]-1,3-thiazine from U.S. Pat. No. 4,031,087.

EXAMPLE A

Phaedon Larvae test

Solvent: 7 parts by weight of dimethylformamide
Emulsifier: 1 part by weight of alkylaryl polyglycol ether:

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, the following compounds of the preparation examples, for example, (11), (13), (15), (16), (35), (37), (38), (39), (41), (42), (43), (44), (45), (46), (52), (53), (54), (55), (57) and (58) exhibit an action of 100% after 3 days at an active compound concentration of 0.01%, whereas the comparison substance (A) exhibits no action.

EXAMPLE B

Plutella test

Solvent: 7 parts by weight of dimethylformamide
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, the following compounds of the preparation examples, for example, (9), (11), (15), (16), (37), (38), (39), (40), (41), (42) and (46) exhibit an action of 100% after 3 days at an active compound concentration of 0.01%, whereas the comparison substance (A) exhibits no action.

EXAMPLE C

Myzus test

Solvent: 7 parts by weight of dimethylformamide
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with the peach aphid (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, the following compounds of the preparation examples, for example, (13), (15), (16), (37), (38), (39), (40), (41), (42), (43), (44), (45) and (46) exhibit an action of 99-100% after 1 day at an active compound concentration of 0.01%, whereas the comparison substance (A) exhibits an action of 40%.

EXAMPLE D

Aphis test (systemic action)

Solvent: 7 parts by weight of dimethylformamide
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the black bean aphid (*Aphis fabae*) are each watered with 20 ml of the preparation of the active compound of the desired concentration in such a way that the preparation of the active compound penetrates into the soil without wetting the shoot. The active compound is taken up by the roots and passes to the shoot.

After the specified periods of time, the destruction in % is determined. 100% means that all the aphids have been killed; 0% means that none of the aphids have been killed.

In this test, the following compounds of the preparation examples, for example, (11), (13), (15), (16), (35), (37), (38), (39), (40), (41), (42), (43), (45), (46), (52), (53), (54), (57) and (58) exhibit an action of 90 to 100% after 4 days at an active compound concentration of 0.01%, whereas the comparison substance (A) exhibits no action.

EXAMPLE E

Critical concentration test/soil insects

Test insect: Phorbia antiqua maggots in the soil
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (= mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, (14) and (16) exhibit an action of 100% at an active compound concentration of 20 ppm, whereas the comparison substance (A) exhibits no action.

EXAMPLE F

Critical concentration test/soil insects

Test insect: Diabrotica balteata larvae in the soil
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (= mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, (14) and (16) exhibit an action of 100% at an active compound concentration of 20 ppm, whereas the comparison substance (A) exhibits no action.

EXAMPLE G

Critical concentration test / root-systemic action

Test insect: Phaedon cochleariae larvae
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (= mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a rurther 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, the following compounds of the preparation examples, for example, (14), (16), (64), (67), (88) and (103) exhibit an action of 100% at an active compound concentration of 20 ppm, whereas the comparison substance (A) exhibits no action.

EXAMPLE H

Critical concentration test / root-systemic action

Test insect: Myzus persicae
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (= mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, the following compounds of the preparation examples, for example, (9), (11), (13), (16), (39), (57), (64), (67), (88) and (103) exhibit an action of 100% at an active compound concentration of 20 ppm, whereas the comparison substance (A) exhibits no action.

EXAMPLE I

Critical concentration test

Test nematode: Meloidogyne incognita
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts and the degree of effectiveness of the active compound is determined in %. The degree of effectiveness is 100% if infestation is completely avoided and is 0% if the infestation is just as high as in the case of the control plants in untreated soil which has been infested in the same manner.

In this test, the following compounds of the preparation examples, for example, (33), (34), (35) and (36) exhibit an action of 100% at an active compound concentration of 20 ppm, whereas the comparison substance (A) exhibits no action.

EXAMPLE J

Test with *Lucilia cuprina* resistant larvae

Emulsifier:
 35 parts by weight of ethylene glycol monomethyl ether
 35 parts by weight of nonylphenol polyglycol ether.

To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm³ of horse muscle and 0.5 ml of the preparation of active compound. After 24 hours, the degree of destruction is determined.

In this test, the following compounds of the preparation examples, for example, (7), (9), (10), (11), (13), (14), (16), (17), (18), (19), (20), (21), (22), (23), (24), (26), (28), (30), (31), (35), (36), (40), (41), (42), (43), (44), (45) and (46) exhibit a destruction of 100% at an active compound concentration of 1000 ppm.

We claim:
1. A 1,2,3,6-Tetrahydro-5-nitro-pyrimidine derivative: of the formula

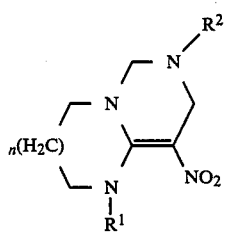

in which
 n represents the numbers 0, 1 or 2,
 $R^1$ represents hydrogen, or alkyl, having 1 to 20 carbon atoms, which is optionally substituted by fluorine, chlorine, bromine, cyano, nitro, hydroxyl, $C_1$–$C_4$-alkoxy, $C_1$–$C_4$-alkylthio, halogeno-$C_1$–$C_2$-alkoxy, halogeno-$C_1$–$C_2$-alkylthio, amino, $C_1$–$C_4$-alkylamino or di-$C_1$–$C_4$-alkylamino; alkenyl and alkinyl each having 2 to 6 carbon atoms; aralkyl, having 6 to 10 carbon atoms in the aryl part and 1 to 4 carbon atoms in the alkyl part, which is optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_2$-alkyl, halogeno-$C_1$–$C_2$-alkoxy or halogeno-$C_1$–$C_2$-alkylthio, or represents furyl-$C_1$–$C_3$-alkyl, thiophenyl-$C_1$–$C_3$-alkyl, pyrazolyl-$C_1$–$C_3$-alkyl, imidazolyl-$C_1$–$C_3$-alkyl, pyrrolyl-$C_1$–$C_3$-alkyl, 1,2,4-triazolyl-$C_1$–$C_3$-alkyl, 1,2,3-triazolyl-$C_1$–$C_3$-alkyl, pyrimidinyl-$C_1$–$C_3$-alkyl, pyrazinyl-$C_1$–$C_3$-alkyl, pyridyl-$C_1$–$C_3$-alkyl, oxazolyl-$C_1$–$C_3$-alkyl, isoxazolyl-$C_1$–$C_3$-alkyl, 1,2,4-oxadiazolyl-$C_1$–$C_3$-alkyl, 1,3,4-oxadiazolyl-$C_1$–$C_3$-alkyl, thiazolyl-$C_1$–$C_3$-alkyl, isothiazolyl-$C_1$–$C_3$-alkyl, 1,2,5-thiadiazolyl-$C_1$–$C_3$-alkyl and 1,3,4-thiadiazolyl-$C_1$–$C_3$-alkyl which are optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkylthio, amino, $C_1$–$C_4$-alkylamino or di-$C_1$–$C_4$-alkylamino, and
 $R^2$ represents dialkylamino having 1 to 6 carbon atoms in each alkyl part; alkoxy having 1 to 6 carbon atoms; alkenyloxy having 3 to 6 carbon atoms; aralkoxy having 6 to 10 carbon atoms in the aryl part and 1 to 4 carbon atoms in the alkyl part, or alkyl, having 1 to 20 carbon atoms, which is optionally substituted by fluorine, chlorine, bromine, cyano, nitro, hydroxyl, mercapto, $C_1$–$C_4$-alkoxy, $C_1$–$C_4$-alkylthio, halogeno-$C_1$–$C_2$-alkoxy, halogeno-$C_1$–$C_2$-alkylthio, amino, $C_1$–$C_4$-alkylamino, di-$C_1$–$C_4$-alkylamino, hydroxycarbonyl, $C_1$–$C_4$-alkoxycarbonyl, $C_1$–$C_4$-alkylcarbonlamino, morpholino or $C_3$–$C_6$-cycloalkyl; alkenyl and alknyl each having 3 to 6 carbon atoms; cycloalkyl, having 3 to 8 carbon atoms, which is optionally substituted by $C_1$–$C_2$-alkyl, fluorine, chlorine, bromine or halogeno-$C_1$–$C_2$-alkyl; aralkyl, having 6 to 10 carbon atoms in the aryl part and 1 to 4 carbon atoms in the alkyl part, which is optionally substituted by fluorine, chlorine, bromine, cyano, nitro, $C_1$–$C_4$-alkyl, $C_1$–$C_4$-alkoxy, $C_1$–$C_4$-alkylthio, halogeno-$C_1$–$C_2$-alkyl, halogeno-$C_1$–$C_2$-alkoxy or halogeno-$C_1$–$C_2$-alkylthio, and also represents furyl-$C_1$–$C_3$-alkyl, thiophenyl-$C_1$–$C_3$-alkyl, pyrazolyl-$C_1$–$C_3$-alkyl, imidazolyl-$C_1$–$C_3$-alkyl, pyrrolyl-$C_1$–$C_3$-alkyl, 1,2,4-triazolyl-$C_1$–$C_3$-alkyl, 1,2,3-triazolyl-$C_1$–$C_3$-alkyl, pyridyl-$C_1$–$C_3$-alkyl, pyrazinyl-$C_1$–$C_3$-alkyl, pyrimidinyl-$C_1$–$C_3$-alkyl, oxazolyl-$C_1$–$C_3$-alkyl, isoxazolyl-$C_1$–$C_3$-alkyl, 1,2,4-oxadiazolyl-$C_1$–$C_3$-alkyl, 1,3,4-oxadiazolyl-$C_1$–$C_3$-alkyl, thiazolyl-$C_1$–$C_3$-alkyl, isothiazolyl-$C_1$–$C_3$-alkyl, 1,2,5-thiadiazolyl-$C_1$–$C_3$-alkyl and 1,3,4-thiadiazolyl-$C_1$–$C_3$-alkyl which are optionally substituted by fluorine, chlorine, bormine, cyano, nitro, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkylthio, amino, $C_1$–$C_4$-alkylamino or di-$C_1$–$C_4$-alkylamino and their acid addition salts.

2. A 1,2,3,6-Tetrahydro-5-nitro-pyrimidine derivative according to claim 1, in which
 n represents the numbers 0 or 1,
 $R^1$ represents hydrogen, or alkyl, having 1 to 12 carbon atoms, which is optionally substituted by fluorine, chlorine, cyano, nitro, hydroxyl, methoxy, ethoxy, methylthio, ethylthio, trifluoromethoxy, difluoromethoxy, trichloromethoxy, chlorodifluoromethoxy, trifluoromethylthio, difluoromethylthio, trichloromethylthio, chlorodifluoromethylthio, amino, methylamino, ethylamino, dimethylamino or diethylamino; alkenyl and alkinyl each having 3 or 4 carbon atoms; benzyl and phenylethyl which are optionally substituted by fluorine, chlorine, bromine, cyano, nitro, methyl, ethyl, methoxy, ethoxy, methylthio, ethylthio, trifluoromethylthio, trifluoromethoxy or trifluoromethylthio, and also represents thiophenylmethyl, pyrazolylmethyl, 1,2,4-triazolylmethyl, pyrazinylmethyl, pyrimidinylmethyl, pyridylmethyl, isoxazolylmethyl, oxazolylmethyl, thiazolylmethyl, 1,2,5-thiadiazolylmethyl or 1,3,4-thiadiazolylmethyl which are optionally substituted by fluorine, chlorine, bromine, cyano, nitro, methyl, ethyl, methoxy, methylthio, trifluoromethyl, trifluoromethoxy, trifluoromethylthio, dimethylamino or diethylamino, and $R^2$ represents dialkylamino having 1 to 4 carbon atoms in each alkyl part; alkoxy having 1 to 4 carbon atoms; 1-prop-2-enyloxy; phenylmethoxy, phenylethoxy; alkyl, having 1 to 12 carbon atoms, which is optionally substituted by fluorine, chlorine, bromine, cyano, nitro, hydroxyl, mercapto, methoxy, ethoxy, methylthio, ethylthio, trifluoromethoxy, difluoromethoxy, trichloromethoxy, chlorodifluoromethoxy, trifluoromethylthio, difluoromethylthio, trichloromethylthio, chlorodifluoromethylthio, amino, methylamino, ethylamino, dimethylamino, diethylamino, hydroxycarbonyl, $C_1$–$C_2$-alkoxycarbonyl, $C_1$–$C_2$-alkylcarbonylamino or $C_3$–$C_6$-cycloalkyl; alkenyl and alkinyl each having 3 or 4 carbon atoms; cycloalkyl, having 3 to 6 carbon atoms, which is optionally substituted by fluorine, chlorine or trifluoromethyl; benzyl and phenylethyl which are optionally substituted by fluorine, chlorine, bromine, cyano, nitro, methyl, ethyl, methoxy, ethoxy, methylthio, ethylthio, trifluoromethyl, trifluoromethoxy or trifluoromethylthio, and also represents furylmethyl, thiophenylmethyl, pyrrolylmethyl, pyrimidinylmethyl, thiazolylmethyl, pyrazolylmethyl, morpholinomethyl or morpholino-n-propyl which are optionally substituted by fluorine, chlorine, bromine, cyano, nitro, methyl, ethyl, methoxy, methylthio, trifluoromethyl, trifluoromethoxy, trifluoromethylthio, dimethylamino or diethylamino.

3. A 1,2,3,6-tetrahydro-5-nitropyrimidine derivative according to claim 1, wherein $n = o$, $R^1$ is 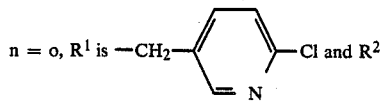 Cl and $R^2$ is selected from the group consisting of cyclohexyl, —$C_{12}H_{25}$—n, —$(CH_2)_9CH_3$, —$(CH_2)_{10}CH_3$ and —$CH_2CH_2OH$.

4. A pesticidal compsition comprising at least one 1,2,3,6-tetrahydro-5-nitropyrimidine derivative according to claim 1 and a suitable extender.

5. A method for combating insects and/or nematodes or to a habitat thereof an insecticidal and/or nematocidal effective amount of at least 1,2,3,6-tetrahydro-5-nitropyrimidine derivative according to claim 1.

* * * * *

UNITED STATES PATENT AND TRADEMARK OFFICE
CERTIFICATE OF CORRECTION

PATENT NO. : 4,831,036
DATED : May 16, 1989
INVENTOR(S) : Wolf et al.

It is certified that error appears in the above-identified patent and that said Letters Patent is hereby corrected as shown below:

| | |
|---|---|
| Col. 2, line 23 | Delete "$\neq$" and substitute -- - -- |
| Col. 7, line 2 | Delete " (III) " |
| Col. 9, line 19 | After " spp., " add -- oryzaephilus surinamensis, anthonomus spp., sitophilus spp., -- |
| Col. 9, line 37 | Delete " Siphoaptera " and substitute -- Siphonaptera -- |
| Col. 37, next to of page for the line count. | After " com- " delete " 65 " move to the center |
| Col. 39, line 5 | Add -- (A) -- |
| Col. 44, line 35 | Delete " alkylcarbonlamino " and substitute -- alkylcarbonylamino -- |

UNITED STATES PATENT AND TRADEMARK OFFICE
CERTIFICATE OF CORRECTION

PATENT NO. : 4,831,036

DATED : May 16, 1989

INVENTOR(S) : Wolf, et al

It is certified that error appears in the above-identified patent and that said Letters Patent is hereby corrected as shown below:

Col. 45, lines 10-11   Delete " trifluoromethylthio " and substitute — trifluoromethyl —

Col. 46, line 31   After " nematodes " add — comprising applying to said insects and/or nematodes —

Signed and Sealed this

Eighteenth Day of December, 1990

Attest:

HARRY F. MANBECK, JR.

Attesting Officer

Commissioner of Patents and Trademarks